US009228025B2

(12) United States Patent
Manion

(10) Patent No.: US 9,228,025 B2
(45) Date of Patent: Jan. 5, 2016

(54) CHICKEN ANTIBODIES THAT BIND TO NANOPARTICLES

(75) Inventor: Michael Keoni Manion, Cronulla (AU)

(73) Assignee: EMPIRE TECHNOLOGY DEVELOPMENT LLC, Wilmington, DE (US)

(*) Notice: Subject to any disclaimer, the term of this patent is extended or adjusted under 35 U.S.C. 154(b) by 401 days.

(21) Appl. No.: 13/695,276

(22) PCT Filed: Mar. 12, 2012

(86) PCT No.: PCT/US2012/028787
§ 371 (c)(1),
(2), (4) Date: Oct. 29, 2012

(87) PCT Pub. No.: WO2013/137854
PCT Pub. Date: Sep. 19, 2013

(65) Prior Publication Data
US 2013/0236398 A1 Sep. 12, 2013

(51) Int. Cl.
*C07K 16/44* (2006.01)
*A61K 39/395* (2006.01)
*G01N 33/68* (2006.01)
*G01N 33/53* (2006.01)

(52) U.S. Cl.
CPC ............. *C07K 16/44* (2013.01); *G01N 33/53* (2013.01); *G01N 33/6854* (2013.01); *C07K 2317/23* (2013.01)

(58) Field of Classification Search
None
See application file for complete search history.

(56) References Cited

U.S. PATENT DOCUMENTS

| 6,593,157 B1 | 7/2003 | Chen et al. |
| 7,494,589 B2 | 2/2009 | Volpato et al. |
| 2005/0069947 A1 | 3/2005 | Erlanger et al. |
| 2005/0095726 A1 | 5/2005 | Fang et al. |

FOREIGN PATENT DOCUMENTS

| JP | EP 0640347 A1 * | 2/1993 |
| KR | WO2009078513 * | 6/2009 |
| WO | WO 03/007881 | 1/2003 |
| WO | WO 2005/049653 | 6/2005 |

OTHER PUBLICATIONS

"Advantages of Chicken IgY," http://www.aveslab.com/resources/advantages-of-chicken-igy; Aves Labs, Inc., 2010, 2 pages.
"Approaches to Safe Nanotechnology, Managing the Health and Safety Concerns Associated with Engineered Nanomaterials," Department of Health and Human Services, Centers for Disease Control and Prevention, National Institute for Occupational Safety and Health, Mar. 2009, Publication No. 2009 125; http://www.cdc.gov/niosh/docs/2009-125/.
Balasubramanyam et al., "In Vivo Genotoxicity Assessment of Aluminium Oxide Nanomaterials in Rat Peripheral Blood Cells Using the Comet Assay and Micronucleus Test," Mutagenesis, 2009, pp. 245-251, vol. 24 (3).
Bhattacharya et al., "Titanium Dioxide Nanoparticles Induce Oxidative Stress and DNA-Adduct Formation but not DNA-Breakage in Human Lung Cells,"Particle and Fibre Toxicology, Jun. 21, 2009, 17 pages, vol. 6.
Billi et al., "Nanotoxicology of Metal Wear Particles in Total Joint Arthroplasty: A Review of Current Concepts," Journal of Applied Biomaterials & Biomechanics, 2010, vol. 8(1), pp. 1-6.
Braden et al., "X-ray crystal structure of an anti-Buckminsterfullerene antibody Fab fragment: Biomolecular recognition of C60," Proc. Natl. Acad. Sci. USA., Oct. 24, 2010, pp. 12193-12197, vol. 97 (22).
Braydich-Stolle et al., "In Vitro Cytotoxicity of Nanoparticles in Mammalian Germline Stem Cells," Toxicol. Sci. Dec. 2005, pp. 412-419, vol. 88 (2).
Buzea et al., "Nanomaterials and Nanoparticles: Sources and Toxicity," Biointerphases, Dec. 2007, MR17-MR71, vol. 2 (4).
"caNanoLab," information was available at website: http://cananolab.nci.nih.gov/caNanoLab/welcome.do in some form no later than Dec. 4, 2011. While no copy of the website as it existed on Dec. 4, 2011 is in Applicant's possession, Applicant has provided a copy of the website that was printed on Jun. 6, 2011.
Certificate of Analysis, "Diesel particulate Matter (Industrial Forklift)," National Institute of Standards & Technology, Mar. 19, 2009, 10 pages, Gaithersburg, Maryland http://www-s.nist.gov/srmors/certificates/view_certGIF.cfm?certificate=2975;.
Chen et al., "Antigenicity of Fullerenes: Antibodies Specific for Fullerenes and Their Characteristics," Proc. Natl. Acad. Sci. USA, Sep. 1998, pp. 10809-10813, vol. 95.
Choksi et al., "Nanoparticles: A Closer Look at Their Dermal Effects," Journal of Drugs in Dermatology, May 2010, pp. 475-481, vol. 9 (5).
Di Virgilio et al., "Comparative Study of the Cytotoxic and Genotoxic Effects of Titanium Oxide and Aluminium Oxide Nanoparticles in Chinese Hamster Ovary (CHO-K1) Cells," Journal of Hazardous Materials, 2010, pp. 711-718, vol. 177.
Dobrovolskaia et al., "Immunological Properties of Engineered Nanomaterials," Nature Nanotechnology, Aug. 2007, pp. 469-478, vol. 2.
Haak-Frendscho, "Why IgY? Chicken Polyclonal Antibody, An Appealing Alternative," Promega Notes Magazine, 1994, p. 11, vol. 46.
Hu et al., "Potential Neurotoxicity of Nanoparticles," International Journal of Pharmaceutics, 2010, pp. 115-121, vol. 394.
"IgY EggsPress Purification Kit," Gallus Immunotech Ltd, information was available at website www.gallusimmunotech.com/IgY-Purification-Kit, in some form no later than Dec. 4, 2011. While no copy of the website as it existed on Dec. 4, 2011 is in Applicant's possession, Applicant has provided a copy of the website that was printed on Oct. 18, 2012.
"International Alliance for NanoEHS Harmonization," information was available at website: http://www.nanoehsalliance.org/ in some form no later than Dec. 4, 2011. While no copy of the website as it existed on Dec. 4, 2011 is in Applicant's possession, Applicant has provided a copy of the website that was printed on Jun. 6, 2011.

(Continued)

*Primary Examiner* — Yunsoo Kim
(74) *Attorney, Agent, or Firm* — Knobbe Martens Olson & Bear LLP

(57) ABSTRACT

Antibodies and antibody fragments that selectively bind to nanoparticles are provided herein.

24 Claims, 18 Drawing Sheets

(56) References Cited

OTHER PUBLICATIONS

Internatidnal Search Report and Written Opinion received for International Application No. PCT/US2012/028787, mailed on May 11, 2012, filed on Mar. 12, 2012.

Itkis et al., "Purity Evaluation of As-Prepared Single-Walled Carbon Nanotube Soot by Use of Solution-Phase Near-IR Spectroscopy," Nano Letters, 2003, pp. 309-314, vol. 3 (3).

Kolosnjaj et al., "Toxicity Studies of Carbon Nanotubes," Adv Exp Med Biol., 2007, pp. 181-204, vol. 620.

Lam et al., "A Review of Carbon Nanotube Toxicity and Assessment of Potential Occupational and Environmental Health Risks," Critical Review in Toxicology, 2006, pp. 189-217, vol. 36.

Larsson et al., "Chicken Antibodies: Taking Advantage of Evolution—A Review," Poultry Science Association, Inc., 1993, pp. 1807-1812, vol. 72 (10).

Li et al., "Nanoparticle-Induced Pulmonary Toxicity," Experimental Biology and Medicine, 2010, pp. 1025-1033, vol. 235.

"Nanotechnology," Centers for Disease Control and Prevention, information was available at website: www.cdc.gov/niosh/topics/nanotech/default.html in some form no later than Dec. 4, 2011. While no copy of the website as it existed on Dec. 4, 2011 is in Applicant's possession, Applicant has provided a copy of the website that was printed on Jun. 6, 2011.

Nanotechnology, Information was available at website: http://www.cdc.gov/niosh/topics/nanotech/NIL.html; while no copy of the website as it existed on Dec. 4, 2011, is in Applicant's possession, Applicant has provided a copy of the website that was printed on Oct. 26, 2012.

Nanotoxicology (from Wikipedia), Information was available at website: http://en.wikipedia.org/wiki/Nanotoxicology; while no copy of the website as it existed on Dec. 4, 2011, is in Applicant's possession, Applicant has provided a copy of the website that was printed on May 18, 2012.

Nel et al. "Toxic Potential of Materials at the Nanolevel," Science, Feb. 3, 2006, pp. 622-627, vol. 311 (5761).

Nelson, "Antibody Fragments, Hope and Hype," Landes Bioscience, Jan./Feb. 2010, 10 pages, vol. 2(1).

Pfau et al., "Asbestos-Induced Autoimmunity in C57B1/6 Mice," Journal of Immunotoxicology, 2008,, pp. 129-137, vol. 5.

"Reliable, High-Yield Purification of Antibodies (IgY) from Chicken Eggs," Thermo Fischer Scientific Inc., 2010, 2 pages; Rockford, Illinois.

Review—Chicken Antibodies; http://www.oramune.com/custom.aspx?id=7; Immune Therapy Research Laboratory, 2004, 3 pages.

Sayes et al, "Correlating Nanoscale Titania Structure with Toxicity: A Cytotoxicity and Inflammatory Response Study with Human Dermal Fibroblasts and Human Lung Epithelial Cells," Toxicological Sciences, 2006, pp. 174-185, vol. 92 (1).

Stern et al., "Nanotechnology Safety Concerns Revisited," Toxicological Sciences, 2008, pp. 4-21, vol. 101 (1).

Takano et al., "Diesel Exhaust Particles Enhance Antigen-Induced Airway Inflammation and Local Cytokine Expression in Mice," Am. J. Respir. Crti. Care Med., 1997, pp. 36-42, vol. 156.

"The Virtual Journal of Nanotechnology Environment, Health and Safety—Special Series in Risk Analysis Journal on 'Perspectives on Risks of Nanomaterials and Nanotechnologies: Advancing the Science,'" information was available at website: http://cohesion.rice.edu/centersandinst/icon/virtualjournal.cfm in some form no later than Dec. 4, 2011. While no copy of the website as it existed on Dec. 4, 2011 is in Applicant's possession, Applicant has provided a copy of the website that was printed on Jun. 6, 2011.

Watanabe et al., "Human Anti-Gold Antibodies Biofunctionalization of Gold Nanoparticles and Surfaces with Anti-Gold Antibodies," The Journal of Biological Chemistry, Dec. 19, 2008, pp. 36031-36038, vol. 283 (51).

"Welcome to the Nanomaterial-Biological Interactions Knowledgebase!" information was available at website: http://nbi.oregonstate.edu/ in some form no later than Dec. 4, 2011. While no copy of the website as it existed on Dec. 4, 2011 is in Applicant's possession, Applicant has provided a copy of the website that was printed on Jun. 6, 2011.

"What is Nanomanufacturing?" information was available at website: http://www.internano.org/ in some form no later than Dec. 4, 2011. While no copy of the website as it existed on Dec. 4, 2011 is in Applicant's possession, Applicant has provided a copy of the website that was printed on Jun. 6, 2011.

Wright et al., "A Diesel Exhaust Filter System for Industrial Diesel Forklifts," SAE Technical Paper Series, International Off-Highway & Powerplant Congress and Exposition, Sep. 9-12, 1991, 11 pages, Milwaukee, Wisconsin.

* cited by examiner

CHICKEN ANTIBODIES THAT BIND TO NANOPARTICLES

CROSS-REFERENCE TO RELATED APPLICATION

This application is the U.S. national phase entry under 35 U.S.C. §371 of PCT/US2012/028787, filed Mar. 12, 2012, the entire disclosure of which is hereby incorporated by reference herein.

FIELD

Embodiments herein generally relate to antibodies and antibody fragments that bind to nanoparticles.

BACKGROUND

Nanoparticles are pervasive in our daily lives, and some of them are very dangerous for human health. Various sources suggest that nanoparticles are taken up by various tissues in the human body, and can potentially cause harm in several ways.

SUMMARY

In some embodiments, isolated antibodies that specifically bind to nanoparticles are provided herein.

In some embodiments, an isolated chicken antibody or binding fragment thereof that specifically binds to a nanoparticle is provided herein.

In some embodiments, an antibody composition including at least one chicken antibody or binding fragment thereof that specifically binds to a nanoparticle and at least one compound selected from an aerosolizing medium, a sprayable medium, a cross-linker, a support surface, a fiber, a foam medium, a nutritionally acceptable carrier, a pharmaceutically acceptable carrier, a magnetic particle, a lotion, or any combination thereof.

In some embodiments, a composition for targeting a nanoparticle for delivery to an immune system, the composition including at least one nanoparticle and at least one chicken antibody or binding fragment thereof that specifically binds to the at least one nanoparticle.

In some embodiments, an array including a support and at least one chicken antibody or binding fragment thereof that binds specifically to a nanoparticle is provided. The at least one chicken antibody or fragment thereof is immobilized on the support.

In some embodiments, a method of screening for at least one IgY antibody that binds specifically to a nanoparticle is provided. In some embodiments, the method includes immunizing a fowl with an immunizing concentration of a nanoparticle, collecting at least one egg from the fowl, and isolating from the egg at least one IgY antibody that specifically binds to the nanoparticle.

In some embodiments, an isolated chicken antibody or binding fragment thereof that selectively binds to a nanoparticle based upon a material of the nanoparticle is provided.

In some embodiments, an isolated chicken antibody or binding fragment thereof that specifically binds to an epitope on a nanoparticulate is provided.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 15($b$) is a graph depicting the results of antibody precipitation of DPM in suspension (normalized values).

DETAILED DESCRIPTION OF THE PREFERRED EMBODIMENT

Figure 1:
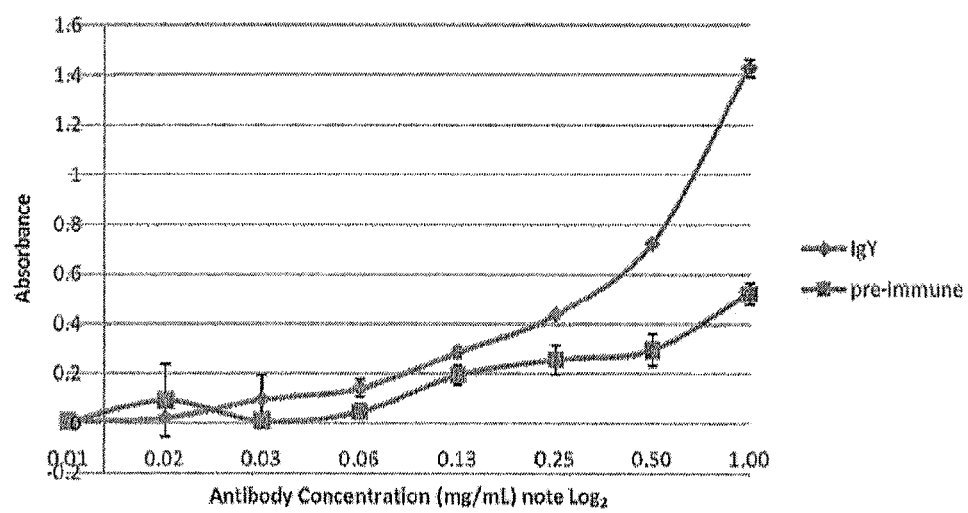
FIG. 1 is a graph depicting the results of anti-$C_{60}$ IgY binding to $C_{60}$ Ag.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Various nanoparticles are increasingly believed to be hazardous to human health when taken-up by human tissue, and can be found in air, water, lotions, or other compositions that come into contact with humans. Examples of nanoparticles include crystalline forms of $TiO_2$, single-walled carbon nanotubes, diesel particulates, asbestos fibers, and $C_{60}$ fullerene. In some embodiments, antibodies that bind to nanoparticles (including one or more of the noted nanoparticles) are provided. In some embodiments, the antibodies can be chicken based antibodies. In some embodiments, compositions including antibodies that specifically bind nanoparticles are provided. Through the binding of antibodies to nanoparticle contaminants, these compositions can remove, immobilize, or immobilize and remove nanoparticles from water, air, and other substances. For example, these compositions can serve as air filters, water filters, surface cleaners, or decontaminants for removing nanoparticles from human environments and/or tissue. In some embodiments, methods are provided for using antibodies against nanoparticles to decontaminate air, water, a food product, or the tissue of a mammal. In some embodiments, methods are provided for making antibodies against nanoparticles.

In some embodiments, at least one isolated antibody (or binding fragment of an antibody) that binds to a nanoparticle is provided. In some embodiments, the antibody or binding fragment selectively binds to a nanoparticle. In some embodiments, the nanoparticle is manmade. In some embodiments, the nanoparticle is one of the nanoparticles noted herein. In some embodiments, the antibody is a fowl antibody. For the sake of brevity, the term "antibody" is used in the specification to denote both full length antibodies and binding fragments thereof. Thus, unless otherwise specified, any disclosure regarding antibodies also denotes the option of binding fragments of antibodies (including antibody fragments such as fragment antigen-binding (Fab), single-chain variable fragments (scFv), third generation (3G), etc.).

In some embodiments, the isolated antibody is in a substantially pure form. In some embodiments, the isolated antibody is part of a composition that is at least about 50%, 70%, 90%, 95%, 97%, or 99% pure from other biological proteins, including any ranges between any two of the listed values. In some embodiments, the isolated antibody is separate from any cells. In some embodiments, the isolated antibody is separated from a chicken or other biological source of the antibody. In some embodiments, the isolated antibody is part of an aqueous solution. In some embodiments, the isolated antibody is part of a serum. In some embodiments, the isolated antibody is lyophilized.

In some embodiments, the antibody is an IgY antibody. In some embodiments, the antibody is an IgM antibody. In some embodiments, the antibody is an IgA antibody. In some embodiments, the antibody is an IgG antibody. In some embodiments, the antibody is an IgE antibody. In some embodiments, the antibody is an IgD antibody. In some embodiments, the term "antibody" encompasses antibody mimetics and/or engineered antibodies, including, but not limited to Small Modular ImmunoPharmaceuticals ("SMIPs"), Fab, F(ab')$_2$ Fab', scFv, di-scFv, etc.

In some embodiments, the antibody or fragment thereof selectively binds to a nanoparticle. In some embodiments, the nanoparticle is a molecule or combination of molecules. In some embodiments, the nanoparticle is an isolated structure. In some embodiments, the nanoparticle contains the epitope for the antibody, but is itself, part of a larger structure.

The nanoparticles can vary in size. In some embodiments, the nanoparticle has a diameter of about 0.1 nanometers, 0.3, 0.5, 0.8, 1, 2, 5, 10, 30, 50, 70, 100, 200, 300, 500, 800, 1000, 1500, 2000, 3000, 5000, 7000, or 10,000 nanometers, including any range between any two of the listed values.

In some embodiments, the nanoparticle includes at least one of a crystalline form of $TiO_2$, a single-walled carbon nanotube, a diesel particulate, an asbestos fiber, a carbon fullerene, a $C_{60}$ fullerene, a $C_{70}$ fullerene, a $C_{76}$ fullerene, a $C_{78}$ fullerene, a $C_{84}$ fullerene, a fullerene of 100 or more carbon atoms, and/or an aluminum oxide.

Several nanoparticles, and properties of these nanoparticles are described in Table 1:

TABLE 1

| Nanoparticle | Properties of some embodiments |
|---|---|
| $C_{60}$ Fullerene "Buckyball" | Densely packed, stable cluster of 60 carbon atoms in icosahedral structure. |
| Single-walled carbon nanotubes (SWCNT) | One atom thick layer of graphene wrapped into a seamless cylinder. Typical diameter around 1 nm with length variable, and bundling common. |
| Diesel Particulate Matter (DPM) | Heterogeneous material including diesel soot (includes carbon nanoparticles of different shapes), and aerosols such as ash particulates, metallic abrasion particles, sulfates and silicates. |
| Aluminum Oxide ($Al_2O_3$) | Widely distributed (naturally occurring and industrially produced) inorganic amphoteric oxide which can adopt many different shapes. Particles can vary in size and, in some embodiments, can have a size distribution of <50 nm. |
| Titanium dioxide ($TiO_2$) | Naturally occurring oxide of titanium, occurs in different crystal forms, and includes, for example, anatase. |
| Asbestos fibers | Naturally occurring silicate minerals with long thin fibrous crystals. In some embodiments, there is significant toxicity, and can include, for example, amosite asbestos. |

In some embodiments, the isolated antibody includes any avian antibody. In some embodiments, the fowl is a chicken, and the antibody is a chicken. In some embodiments, the antibody composition is a polyclonal antibody. In some embodiments, a mixture of antibodies from two or more hosts of the same species is provided. In some embodiments, a mixture of antibodies from hosts of two or more different species is provided. It is noted that "avian antibodies," "chicken antibodies," etc., need not denote that the antibody itself is purified from a bird or chicken. Instead, this denotes that the sequences within the antibody are avian or chicken sequences. In some embodiments, the antibody need not be avian, and can instead be human, mouse, rat, porcine, rabbit, and/or other in sequence.

In some embodiments, the antibody is a monoclonal antibody.

In some embodiments, the antibody is chimeric. In some embodiments, the isolated antibody includes at least one region of a chicken antibody. In some embodiments, the antibody includes at least one region of an antibody from a non-chicken host, and at least one region from a chicken host. In some embodiments, the "region" from the chicken (or the region that is avian) can be at least one of the following: Fc, Fab, CH2, CH3, heavy chain CDR1, heavy chain CDR2, heavy chain CDR3, light chain CDR1, light chain CDR2, light chain CDR3, heavy chain variable region, light chain variable region, heavy chain FR1, heavy chain FR2, heavy chain FR3, heavy chain FR4, light chain FR1, light chain FR2, light chain FR3, and/or a light chain FR4. In some embodiments, one or more of the CDRs is chicken based (e.g., 1, 2, 3, 4, 5, or 6 of the CDRs are avian and/or chicken sequences). In some embodiments, the antibody includes a chicken heavy chain. In some embodiments, the antibody includes at least one of a heavy chain chicken framework region 1, a heavy chain chicken framework region 2, a heavy chain chicken framework region 3, a heavy chain chicken framework region 4. In some embodiments, the antibody includes a chicken constant domain. In some embodiments, the antibody includes a chicken variable domain. In some embodiments, the antibody includes a chicken constant domain and a chicken variable domain. In some embodiments, the antibody includes at least one of a heavy chain framework region 1, heavy chain framework region 2, heavy chain framework region 3, heavy chain framework region 4, constant domain, or variable domain of a non-chicken host. Examples of non-chicken hosts include goat, sheep, camel, horse, donkey, cow, pig, rabbit, mouse, hamster, and guinea pig. In some embodiments, the antibody can be a humanized antibody with 1, 2, 3, 4, 5, or 6 chicken CDR's.

In some embodiments, a chicken antibody is provided that binds to a nanoparticle based on a property of a nanoparticle. In some embodiments, the property is a material of a nanoparticle. In some embodiments, the property is a shape or conformation of a nanoparticle. In some embodiments, an antibody binds selectively to a material of a nanoparticle. In some embodiments, the material of nanoparticle is carbon. In some embodiments, the material of a nanoparticle is silicate. In some embodiments, the material is a metal oxide. In some embodiments, the material is a titanium oxide. In some embodiments, the material is an aluminum oxide. In some embodiments, the antibody binds selectively to a combination of at least two materials of the nanoparticle. In some embodiments, the antibody binds selectively to a shape or conformation of a nanoparticle. In some embodiments, the shape is a three-dimensional shape of the nanoparticle. In some embodiments, the shape is a three-dimensional shape of a structure containing two or more nanoparticles. In some embodiments, the antibodies are generally regarded as safe ("GRAS"), edible, and/or orally available.

In some embodiments, the nanoparticulate is a single nanoparticle. In some embodiments, the nanoparticulate is part of a larger structure. In some embodiments, the nanoparticle has the epitope for the antibody, but is part of the larger structure. In some embodiments, the larger structure includes one or more of the herein listed molecules. In some embodiments, the larger structure includes two or more of the above-listed molecules. In some embodiments, the larger structure two or more of the same molecule. In some embodiments, the larger structure includes two or more different molecules. In some embodiments, the larger structure has a diameter of about 0.5, 1, 3, 5, 10, 50, 80, 100, 200, 300, 500, 800, 1000, 1500, 2000, 3000, 5000, 7000, 10,000, 13,000, 17,000, 20,000, 25,000, 30,000, 40,000, 50,000, 70,000, 100,000, 150,000, 200,000, 300,000, or 500,000 nanometers, including any ranges between any two of the listed values.

In some embodiments, antibody compositions are provided. In some embodiments, an antibody composition includes at least one isolated antibody that specifically binds to a nanoparticle. In some embodiments, the antibody composition includes two or more isolated antibodies or binding fragments of antibodies or a combination of antibodies and binding fragments, each of which specifically binds to the same nanoparticle, e.g., 2, 3, 4, 5, 6, 7, 8, 9, 10, 50, 100, 200, or more different types of antibodies, including any range above any one of the preceding values. In some embodiments, an antibody composition includes at least one antibody that specifically binds to a first nanoparticle epitope, and at least one antibody that specifically binds to a second nanoparticle epitope. In some embodiments, the antibody composition includes three or more antibodies, each of which specifically binds to a different nanoparticle.

In some embodiments, an antibody composition includes at least one additional ingredient. In some embodiments, the additional ingredient is at least one of an aerosolizing medium, a sprayable medium, a cross-linker, a support surface, a fiber, a foam medium, a pharmaceutically acceptable carrier, a lotion, and/or a nutritionally acceptable carrier including, for example, food and/or beverages, mouthwash, lozenges, items for ingestions, and/or items that are generally regarded as safe (GRAS). In some embodiments, the antibody composition includes two or more of the listed additional ingredients.

In some embodiments, the antibody composition includes at least one isolated antibody that specifically binds to a nanoparticle, and a support surface. Thus, in some embodiments, the antibody can be part of a device. In some embodiments, at least one antibody is immobilized on the support surface. In some embodiments, the antibody is cross-linked to the support surface. In some embodiments, the antibody is embedded in the support surface. In some embodiments, the antibody is covalently tethered to the support surface. In some embodiments, the antibody includes a magnetic material, and is immobilized on the support surface by an electromagnetic force. In some embodiments, the antibody includes (and/or is attached to) a binding partner of a molecule that is on the support surface, and is immobilized on the support surface through the association of the molecule and its binding partner. In some embodiments, the antibody includes a ligand of a receptor on the support surface, and is immobilized on the support surface through the binding of the ligand and receptor. In some embodiments, the antibody can be associated and/or immobilized on the support surface in any number of ways. In embodiments in which a liquid is present, the antibody need not be immobilized in all embodiments. Thus, for example, if a wet filter is present, the antibody can be contained within the solution and/or the wet filter.

In some embodiments, the support surface is configured to permit gas to pass by the antibody or antibodies (such as in a filter, as noted below). In some embodiments, the support surface is configured to permit fluid to pass by the antibody or antibodies. In some embodiments, the support surface is permeable to gas and/or fluid. In some embodiments, the support surface is configured so as to allow gas, fluid, or gas and fluid to flow through the support surface. In some embodiments, the antibody binds to one or more nanoparticle in the gas or fluid, removing the nanoparticle or nanoparticles from the gas or fluid, and thus filtering the gas or fluid. In some embodiments, the gas is air. In some embodiments, the fluid is water. In some embodiments, at least some percentage of the nanoparticles can be removed, e.g., 1, 2, 3, 4, 5, 10, 15, 20, 25, 30, 40, 50, 60, 70, 80, 90, 95, 98, 99, 99.9, 99.99, or 100% of the relevant nanoparticles are removed including any range between any two of the preceding values. In some embodiments, the removal can be selective, so that the percent of nanoparticles removed is at least one of: a metal oxide, a crystalline form of $TiO_2$, a carbon nanoparticle, a single-walled carbon nanotube, a diesel particulate, a silicate nanoparticle, an asbestos fiber, and a $C_{60}$ fullerene.

In some embodiments, the support surface is part of a filter. In some embodiments, the filter is permeable to at least one nanoparticle although the presence of the relevant antibody can effectively result in the trapping of the nanoparticle, even though it might otherwise be able to physically pass through the system. In some embodiments, the filter has a pore size of about 0.1 nanometers, 0.3, 0.5, 0.8, 1, 2, 5, 10, 30, 50, 70, 100, 200, 300, 500, 800, 1000, 1500, 2000, 3000, 5000, 7000, 10,000, 20,000, 30,000, 50,000, 100,000, 200,000, or 500,000 nanometers, including any ranges between any two of the listed values or any range above any one of the listed values.

In some embodiments, an antibody-containing solution is used to apply the antibody to a membrane or to a filter. In some embodiments, the membrane or filter would be soaked in the aqueous, antibody containing solution, allowing the antibody to attach and/or associate with the filter. An evaporation stage can facilitate this in some embodiments. In some embodiments, an adhesive, such as Protein A, is attached to the filter or membrane, in order to capture the antibody onto the filter/membrane. In some embodiments, mild oxidation of IgY or another immunoglobulin or an immunoglobulin fragment with sodium periodate will produce reactive aldehydes on the carbohydrate moieties of the Fc portion that then can be alkylated by hydrazides. This approach is advantageous for antibodies because they become covalently modified in a manner that maintains immunological reactivity, and it is ideal for polyclonal antibodies because they are typically heavily glycosylated.

In some embodiments, the filter is integrated into another device, such as a water filter, face mask, or cigarette filter to allow for decontamination of nanoparticles prior to inhalation or ingestion by a person.

In some embodiments, the filters can also be used with bed filters with antibodies or binding fragments attached, or made as columns by attaching antibodies or binding fragments to beads, or using anti-IgY (or other appropriate immunotype) labeled beads to capture the primary antibodies.

In some embodiments, the antibodies are embedded into a mask for filtering airborne nanoparticles from being inhaled. This can be particularly useful, for example, in settings where people are exposed to high levels of a particular set of nanoparticles, (for example, for workers who are subjected to diesel emissions).

In some embodiments, an antibody composition includes at least one isolated antibody that specifically binds to a nanoparticle, and a pharmaceutically acceptable carrier. In some embodiments, the pharmaceutically acceptable carrier facilitates the delivery of the antibody to a human tissue or tissues. In some embodiments, the human tissue or tissues contain at least one nanoparticle that can be specifically bound by at least one antibody of the antibody composition. For example, a nanoparticle may have been ingested or inhaled. In some embodiments, the antibody composition includes two or more pharmaceutically acceptable carriers. In some embodiments, the composition is packaged as a lozenge, a candy, a chewing gum, a mouthwash, or a mouth spray.

In some embodiments, the antibody is dissolved in the pharmaceutically acceptable carrier, for example in a mouthwash or mouth spray. In some embodiments, the antibody is dissolved in an aqueous solution of the pharmaceutically acceptable carrier. In some embodiments, the aqueous solution can be adjusted to facilitate antibody stability and/or solubility. In some embodiments, the antibody-containing solution, for example an IgY solution, is formulated as a lollipop, or lozenge or a chewing gum which is held in the mouth cavity allowing the antibody to be absorbed through the mucosal lining of the mouth.

In some embodiments, the antibody composition includes at least one flavoring agent. A flavoring agent may assist with compliance. In some embodiments, the antibody composition includes at least one buffer. In some embodiments, the antibody composition is enterically coated.

In some embodiments, a therapeutically effective amount of the antibody is provided with pharmaceutical carrier. For example, IgY is known to be deliverable orally and to provide a significant level of passive immunity. In some embodiments, the IgY can be formulated against nanoparticles, such as diesel soot, cigarette smoke particles, or other contaminants, and packaged as a lozenge. The person exposed to the nanoparticle of interest could then suck on the lozenge to release an appropriate amount of antibody to bind the nanoparticle, and thus increase their clearance, and reduce their harmful effects.

In some embodiments, a composition for targeting a nanoparticle for delivery to an immune system is provided. In some embodiments, the composition includes at least one nanoparticle and at least one isolated antibody that specifically binds to the at least one nanoparticle. In some embodiments, the antibody is bound to the nanoparticle or nanoparticles. In some embodiments, the nanoparticle is substantially coated by antibodies and/or binding fragments. In some embodiments, the composition is administered to a mammal. Immune cells such as macrophages can recognize antibodies or antibody fragments bound to a nanoparticle or nanoparticles, and phagocytose them, thus delivering the nanoparticle or nanoparticles to the immune system.

In some embodiments, an antibody composition includes an array. In some embodiments, the array includes at least one support. In some embodiments, the support is a membrane. In some embodiments, the support is a tube or channel. In some embodiments, the support is substantially impermeable to liquid. In some embodiments, the support is substantially impermeable to gas. In some embodiments, the array includes at least one isolated antibody that binds specifically to a nanoparticle. In some embodiments, the isolated antibody is immobilized on the support. In some embodiments, the antibody is reversible immobilized on the support, and can be released from the support. In some embodiments, at least part of the antibody is embedded it the support. In some embodiments, the array includes at least a first antibody that specifically binds to at least a first nanoparticle, and at least a second antibody that specifically binds to at least a second nanoparticle. In some embodiments, the array includes multiple antibodies or populations of antibodies, each of which binds specifically to a different nanoparticle. In some embodiments, the array includes a solution for transporting nanoparticles in the array. In some embodiments, the array includes a solution for dissociating bound nanoparticles from antibodies or binding fragments. In some embodiments, bound nanoparticles are reversibly dissociated from antibodies or binding fragments. In some embodiments, the array includes a solution for dissociating antibodies or binding fragments from the support.

In some embodiments, the array is used in biological computing applications. For example, by embedding antibodies against a particular nanoparticle in a particular area of the array, this provides a method to reversibly bind a nanoparticle in a particular place, which can be inside a microfluidic cell, or chip. The nanoparticle can have semiconductor, or other catalytic activity (e.g. $TiO_2$ is a photocatalyst). Such activity can then be localized to where the antibody is immobilized, and then released upon un-binding. In some embodiments, the antibody binding alters a property of the nanoparticle. In some embodiments, the property may be an electrical property. In some embodiments, the property may be the absorption and/or emission of EM radiation, such as light. In some embodiments, the property may be a physical property, such as the elasticity or hardness of the nanoparticle. In some embodiments, the property may be a chemical property, such as catalytic activity. In some embodiments, the change in the property of the nanoparticle is used as a signal for computing.

In some embodiments, a method of screening for at least one isolated antibody that binds specifically to a nanoparticle is provided. In some embodiments, the method includes immunizing a host with an immunizing concentration of a nanoparticle. In some embodiments, the method includes collecting antibody-containing material from the host. In some embodiments, the method includes isolating from the antibody-containing material at least one antibody that specifically binds to the nanoparticle.

Figure 17:
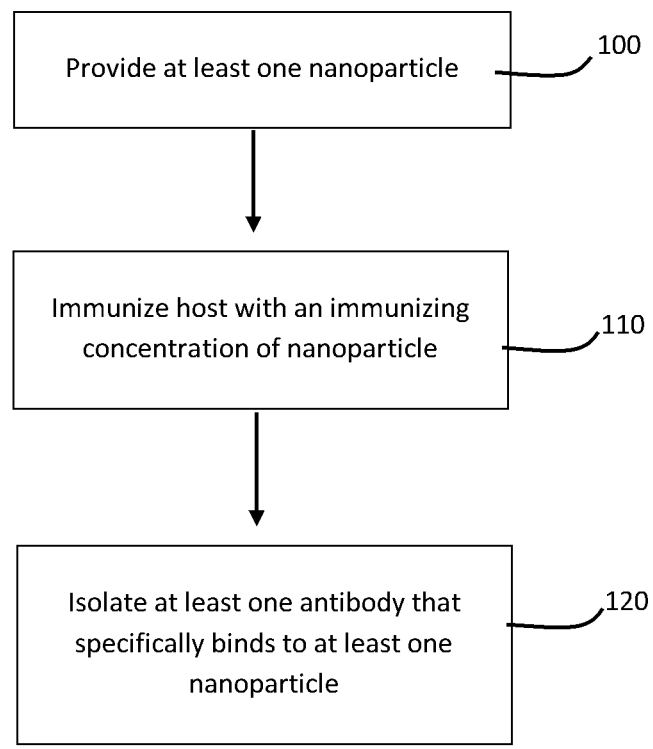
FIG. 17 is a flow chart depicting some embodiments of a method for making the present antibodies or fragments thereof.

FIG. 17 illustrates some embodiments of a method of obtaining an antibody. In some embodiments, at least one nanoparticle is provided 100. In some embodiments, a host (which can be, but need not be, a chicken) is immunized with an immunizing concentration of nanoparticle 110. In some embodiments, at least one antibody that specifically binds to at least one nanoparticle is isolated 120. In some embodiments, isolation can be achieved by taking a sample from an egg from the animal that was immunized and screening it through a filter to which the nanoparticle in question is attached, allowing any antibodies to bind to the filter.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

In some embodiments, a method of producing at least one isolated antibody that binds specifically to a nanoparticle is provided. In some embodiments, the method includes immunizing a fowl with an immunizing concentration of a nanoparticle. In some embodiments, the fowl is a chicken. In some embodiments, two or more fowl are immunized. In some embodiments, the immunizing concentration of a nanoparticle is about 0.1 mg/mL, 0.2, 0.3, 0.5, 1, 1.2, 1.5, 2, 3, 5, 10, or 20 mg/mL, including any ranges between any two of the stated values. In some embodiments, the immunizing includes injecting the fowl with about 0.3, 0.5, 1, 1.3, 1.5, 2, 3, 5, or 10 mL of nanoparticle-containing solution. In some embodiments, the nanoparticle-containing solution contains at least one adjuvant. In some embodiments, nanoparticle-containing solution is injected into the fowl. In some embodiments, the nanoparticle-containing solution is injected into the fowl at two or more times, for example on a first day and on a second day. In some embodiments, each injection is about 1 day, 2, 3, 5, 10, 12, 15, or 20 days after the previous injection.

In some embodiments, the method includes collecting at least one egg from the fowl. In some embodiments, the egg or egg is stored for a period of time. In some embodiment the yolk or yolks are collected and stored for a period of time.

In some embodiments, the method includes isolating from the egg or eggs at least one antibody. In some embodiments, material from the egg or eggs is combined. In some embodiments, a solution enriched in antibody is obtained from the egg or egg. In some embodiments, the solution is a substantially pure solution of antibody. In some embodiments, the solution is at least about 20%, 30%, 40%, 50%, 60%, 70%, 80%, 83%, 85%, 87%, 90%, 92%, 95%, 97%, or 99% pure, including any ranges between any two of the listed values and any range above any one of the preceding values. In some embodiments, the antibody is stored in solution. In some embodiments, the antibody is lyophilized. In some embodiments, the method includes isolating, from an offspring of an immunized hen (either directly from the offspring and/or from the eggs of the offspring).

Provided below is some additional, nonlimiting, information on each of several types of nanoparticles. In some embodiments, the antibodies or fragments thereof bind selectively to one or more of these nanoparticles. In some embodiments, the antibodies bind to other nanoparticles. In some embodiments, the antibodies bind to these nanoparticles selectively compared to binding to other nanoparticles. In some embodiments, the antibodies bind to one of these listed nanoparticles compared to another one or more of the listed nanoparticles.

$C_{60}$ Fullerene Buckyball

Carbon vapor preferentially condenses into an exceedingly stable cluster with 60 carbon atoms ($C_{60}$). The 60 atoms were arranged as the vertices of a truncated icosahedron. Other fullerenes are also known, and include 70, 76, 78, 84 and even over 100 atoms per molecule (and no hydrogen atoms).

While fullerenes are thought not to be toxic, their inclusion in this list immunogens is to test the hypothesis that an antibody can be raised against this particular epitope (i.e. the spherical shape defined by these carbons). Furthermore, since fullerenes are incorporated into many different products, there are benefits in having antibodies against this shape in order to supplement product development opportunities, as well as develop sensor technologies for detecting their presence.

Single-walled carbon nanotubes (SWCNT)

Single-walled carbon nanotubes (SWCNTs) are present in nanoelectronics, field emission displays, and nanostructural composites. Parameters such as structure, size distribution, surface area, surface chemistry, surface charge, and agglomeration state as well as purity of the samples, have considerable impact on the reactivity (e.g., toxicity) of carbon nanotubes. However, available data clearly show that, under some conditions, nanotubes can cross membrane barriers, which suggests that if raw materials reach the organs they can induce harmful effects such as inflammatory and fibrotic reactions.

Results of rodent studies collectively show that regardless of the process by which CNTs were synthesized and the types and amounts of metals they contained, CNTs were capable of producing inflammation, epithelioid granulomas (microscopic nodules), fibrosis, and biochemical/toxicological changes in the lungs.

Since single-walled carbon nanotubes are merely a structural rearrangement of fullerenes into a cylindrical shape, by testing the cross-reactivity of IgY's against each option, the present disclosure provides an indication of the shape discriminatory ability of the system.

The specific single walled carbon nanotube used in the Examples are described by Itkis, et al., however, the Examples use a polyethylene glycol functionalized version, since they are water soluble and long lasting in vivo. These nanotubes are 1.4 nm in diameter and 5-6 micrometers long in 4-5 nanometer bundles. These are available from Sigma Aldrich.

Diesel Particulate Matter

The above two nanoparticles are, amongst other things, typically present in emissions from diesel engines. However, there is considerably more heterogeneity in these emissions, all of which contribute to the toxicity profile of this material. The graphene-based particles have greater shape diversity, and there are also many other types of chemicals present, particularly the polycyclic aromatic hydrocarbons. In some embodiments, although not every particle present will be immunogenic, the chicken's immune response will identify more than one of the particles present in the diesel particular matter as being foreign, and raise an antibody response.

The particular material used in the Examples below, is the NIST Standard Reference Material SRM 2975. The diesel particulate material used to prepare SRM 2975 was obtained from M. E. Wright of the Donaldson Company, Inc., Minneapolis, Minn. The material was collected from a filtering system designed specifically for diesel-powered forklifts.

Asbestos Fibers

At some point in their lives, nearly all humans have been exposed to asbestos in the air they breathe and the water they drink; from natural deposits in the earth, and from the deterioration of asbestos products around us. Six minerals are defined by the United States Environmental Protection Agency as "asbestos" including that belonging to the serpentine class chrysotile and that belonging to the amphibole class amosite, crocidolite, tremolite, anthophyllite and actinolite. The main difference between these two classes is the structure, with the serpentine class having a curly structure, and the amphibole forming long needle-like structures. The amphiboles such as amosite and crocidolite are the most dangerous forms of asbestos due to their long persistence in the lungs after inhalation leading to accumulative effects. Embedding in the lung causes fibrosis (asbestosis) and later malignant changes, with strong associations to mesothelioma.

Most respirable asbestos fibers are invisible to the unaided human eye because their size is about 3.0-20.0 μm long and can be as thin as 0.01 μm.

One of the most dangerous forms of asbestos is amosite (brown asbestos) and it is the second most commonly found form of asbestos in building materials, accounting for about 5% of all asbestos used in factories and other commercial buildings. Its color comes from the natural presence of iron and magnesium found in this form of asbestos. Therefore, the Examples test the ability of the chicken IgY system to generate antibodies to asbestos fibers to the amosite form. These antibodies can also be tested on other forms of asbestos.

Aluminum Oxide

Aluminum oxide is the family of inorganic compounds with the chemical formula $Al_2O_3$. It is an amphoteric oxide and is commonly referred to as alumina, corundum as well as many other names, reflecting its widespread occurrence in nature and industry. Its most significant use is in the production of aluminum metal. Alumina is a favored filler for plastics. Alumina is a common ingredient in sunscreen and antiperspirants.

There is significant debate as to the toxicity profile of alumina nanoparticles, with several studies showing toxicity both in vitro and in vivo. Furthermore, alumina nanoparticles have been demonstrated to be able to cross the blood brain barrier, and accumulate in the brain. While not conclusive, there is accumulating data to suggest that the accumulation of alumina in the brain can be associated with neurodegenerative diseases such as Alzheimer's disease.

The particular source of Aluminum oxide nanoparticles used in the Examples is the Sigma Aldrich product with a size distribution of <50 nm.

Titanium Dioxide

Titanium dioxide ($TiO_2$), also known as titanium (IV) oxide or anatase, is the naturally occurring oxide of titanium. It is also one of the most commercially used forms. At present, there is some evidence for limited toxicity of these particles. Studies had established these nanoparticles to be mainly non-cyto- and -genotoxic, although they had been found to generate free radicals both acellularly (especially through photocatalytic activity) and intracellularly. Given the prevalence of $TiO_2$ NPs, especially in products such as sunscreens and food coloring, there is considerable caution around these, and continual monitoring by agencies such as the FDA and TGA.

The extent to which nanoscale titania affects cellular behavior is not dependent on sample surface area; smaller nanoparticulate materials have effects comparable to larger nanoparticle materials. What does correlate strongly to cytotoxicity, however, is the phase composition of the nanoscale titania. Anatase $TiO_2$, for example, is 100 times more toxic than an equivalent sample of rutile $TiO_2$. Given this, the Examples use $TiO_2$ anatase particles (<25 nm) from Sigma Aldrich.

Examples of nanoparticles which can be of interest are those liberated by combustion (e.g. cigarette smoke or soot from diesel), particles which exist naturally but are released (e.g. asbestos fibers, volcanic eruptions) or manufactured nanoparticles (e.g. fullerenes, carbon nanotubes and nanoparticle metal oxides, amongst others).

Preparation of Nanoparticles for Immunization

In some embodiments, the nanoparticles of interest are concentrated to an appropriate range such that they will be immunogenic to the hen (typically 20-S00f-Lgper immunization). In some embodiments, the nanoparticles are conjugated to an immunogenic protein, such as bovine thyroglobulin. In some embodiments, the nanoparticles are formulated together with an adjuvant, such as complete Freund's adjuvant, in order to raise an immune response in the hen.

In some embodiments, one or more types of nanoparticle can be used to immunize hens to produce a polyclonal response. Due to differences in the immunogenicity of different nanoparticles hens can be immunized with different mixes or individual types of nanoparticles, and the IgY purified from the eggs can then be pooled.

In some embodiments, standard immunization procedures are used, which are well described in the literature. For example, generally between 20-500 micrograms of a nanoparticle or mixture, is blended with complete Freund's adjuvant, and injected intramuscularly into the chicken, generally a few months old. Specific antibody titer can be boosted with two or three additional injections at two week intervals. Eggs are then collected.

Eggs can be kept for up to one year at 4 degrees Celsius prior to IgY purification. Egg yolks are collected, and homogenized. They are diluted in an aqueous solution, such as Phosphate Buffered Saline (PBS). This can be mixed thoroughly to disperse the egg yolk. This solution can then be centrifuged or allowed to stand. The aqueous solution containing the antibodies can then be separated from the lipid phase. The IgY can be precipitated, or purified, for example on a Protein A affinity column, if desired.

Formulation

In some embodiments, the antibody is not further purified, although titration to appropriate levels for use may be likely. Titration can involve either concentrating, or diluting the solution. In some embodiments, the solution can be lyophilized to concentrate the antibody and provide a dry powder for use.

Flocculant

In some embodiments, the antibody is formulated as a flocculant. In some embodiments, a flocculant is made with the antibodies via derivatization. In some embodiments, the antibody can be provided to contaminated water. In some embodiments, the antibody is crosslinked, effectively removing the nanoparticle through precipitation. In some embodiments, filtration is performed to remove the precipitate from the solution.

In some embodiments, these antibodies can be used as a flocculant, either by themselves, or in conjunction with crosslinkers, conjugates (such as magnetic particles or agarose beads), or anti-IgY antibodies, to effectively remove particular nanoparticles from solution. The antibodies can be prepared as described above, as in other methods, or lyophilised, and added as a powder to solution containing a nanoparticle. The bound nanoparticles can settle out of solution, or can be removed by centrifugation, or filtration. This can be particularly useful to provide for ultrapure solutions, or to remove a specific nanoparticle from a mixture.

Sprays

In some embodiments, the antibody is formulated as an aerosol spray. In some embodiments, the aerosol spray includes an aerosolizing agent. In some embodiments, the aerosolized spray is formulated to deliver at least one antibody to contact and bind at least one aerosolized nanoparticle. In some embodiments, upon binding to the aerosolized nanoparticle, the antibody or antibody increases its effective size, and thus removes the nanoparticle from the air. In some embodiments, the aerosol spray is provided in a spray bottle. In some embodiments, the aerosol spray is provided in an aerosol can. In some embodiments, aerosolization is performed by fluidizing the antibody in an appropriate solution, which will depend on the derivatization and intended use of the aerosol. This fluidized solution can then propelled, such as by placing it under pressure using a propellant gas. In some embodiments, the aerosol spray is formulated to provide vapor particles upon aerosolization. In some embodiments, the vapor particles provide a visual indicator of the action and direction of the spray for the user.

In some embodiments, the antibody composition is formulated as a spray to be applied to a surface and then wiped off the surface. In some embodiments, the spray includes a fluid that evaporates readily upon contacting the surface. In some embodiments, the spray is applied to a surface containing at least one nanoparticle, thus delivering at least one antibody to the surface. In some embodiments, the surface is wiped after an incubation time that permits the antibody to bind to the nanoparticle or nanoparticles of the surface.

Foams

In some embodiments, the antibody is formulated as a foam. In some embodiments, the antibody is formulated as a wet spray. In some embodiments, the foam or wet spray is used to decontaminate surfaces that may be contaminated by nanoparticles. By way of example, such a foam or wet spray could be used for ultrapure situations, such as cleanrooms, to ensure highly decontaminated surfaces.

Sunscreens $TiO_2$ is used quite commonly in sunscreen, and it has been shown to increase free radicals intracellularly, which could cause longer term damage. In some embodiments, sunscreen is formulated with antibodies or binding fragments against $TiO_2$, which can reduce this free radical formation as the antibody or fragment can prevent the uptake of the nanoparticles into cells. In some embodiments, the antibodies are used in a soap to remove sunscreen after use, thus ensuring thorough removal of $TiO_2$ nanoparticles from the skin.

Sensors

Antibodies which are specific for nanoparticles provide a basis for sensors and detection methods for determining the presence of the nanoparticle. For example, a dipstick test can be made and performed using the antibody to test for the presence of a particular nanoparticle in solution, or in a sample. In some embodiments, using methods such as the ELISA test, even very low levels of nanoparticles can be detected using these antibodies in a quantitative manner.

Diagnostics

In some embodiments, specific antibodies against nanoparticles can provide for an effective approach to detecting their presence in a tissue sample, which can have significant utility in pathology. For example, a significant problem has arisen with implanted devices that produce toxic nanoparticles as they wear down inside the body. These antibodies can be the basis of a diagnostic to monitor for the presence of such nanoparticles in a patient to alert the patient or a medical care provider before the levels exceed a certain threshold.

Purification

In some embodiments, antibodies against nanoparticles provides for an approach to purify them from a mixed solution. This can be used in a number of contexts. For example, nanoparticles precious metals, such as rare earth minerals, can be used to accumulate these materials in a mixed solution. The materials can be readily recovered after washing by unbinding from the antibody using a chaotropic agent, or by degrading the antibodies using proteases or other approaches.

Magnetic Particles

In some embodiments, the antibody composition includes a magnetic particle. In some embodiments, the antibody is derivatized with a magnetic particle. Examples of magnetic particles include the basic Fe oxides (magnetite and $Fe_2O_3$) or various transition metal ferrites. In some embodiments, derivatizing the antibody with a magnetic particle allows simple removal of the antibody-nanoparticle conjugate from a solution, by applying a magnetic field.

In some embodiments, a magnetic derivatization of the anti-nanoparticle antibody is used to separate a bound nanoparticle from solution. In some embodiments, at least one anti-nanoparticle antibody (for example IgY), which includes a magnetic particle is provided to a solution. In some embodiments, the solution contains and at least one nanoparticle. In some embodiments, the solution is mixed, thus mixing the antibodies and nanoparticles. In some embodiments, the antibodies bind to at least some of the nanoparticles in the solution. In some embodiments, a magnetic field is applied to the solution. Since the antibodies include magnetic particles, the magnetic field can be used to separate the nanoparticle-bound antibody from solution.

Other Derivatizations of Antibodies or Binding Fragments

In some embodiments, the antibody, for example an IgY, can be derivatized in other ways, such as with a biocidal agent such as a halogenated molecule such as chlorine. This provides a directed decontamination to the nanoparticle. Other forms can include derivatization with a pyrophoric agent, and/or free-radical generator, to provide a destructive incendiary and/or redox effect to a nanoparticle upon binding. For example, the antibody may be conjugated to a small amount of white phosphorous, which will spontaneously ignite in air. This ignition could be used to destroy the bound nanoparticle to which the antibody is bound.

In some embodiments, using chicken based antibodies allows for a cost effective approach for producing high-affinity, high-specificity agents for the effective removal of nanoparticle contaminants. The IgY concentration in the yolk is similar to that of the serum levels in the hen, which is usually 6-13 mg/ml. Each yolk is approximately 15 ml, therefore, each hen can produce 450-1170 mg of antibody per week. Purification of antibodies from egg yolks is relatively straightforward and does not require any specialized equipment or reagents. Typically, the eggs are solubilized in an aqueous solution, mixed, and the lipid and aqueous phases allowed to separate. Centrifugation can be used to facilitate this separation phase. The antibodies parse into the aqueous phase. This can then be concentrated, diluted or formulated in various ways.

In some embodiments, the use of IgY antibodies provides for further advantages. Such antibodies are relatively stable even at room temperature, amenable to manipulation and derivatization, and are safe for use in humans. In fact, unlike mammalian antibodies, IgY does not induce the complement system, therefore is ideally suited to provide repeated use such as for prophylactic treatment to prevent disease.

In some embodiments, the amount of antibody added to any of the compositions provided herein can vary depending upon the use. In some embodiments, one can use 1 mg to 100 mg, e.g., 1, 2, 3, 4, 5, 6, 7, 8, 9, 10, 15, 20, 25, 30, 40, 50, 60, 70, 80, 90, or 100 mg per dose. In some embodiments, the amount can be between 1 ng and 10 grams per product, e.g., 1 ng, 10 ng, 100 ng, 1000 ng, 0.01 mg, 0.1 mg, 1 mg, 10 mg, 100 mg, 1 g, 10 g, 100 g, 1 kg, 10 kg, 100 kg, or 1000 kg including any range defined between any two of the preceding values.

In some embodiments, depending on the specificity of the anti-nanoparticle IgY and the formulations made, this technology can be used to address airborne nanoparticle contaminants, water, or even nanoparticle contamination which has been inhaled or ingested.

EXAMPLES

Example 1

Molecular Methods

The present example outlines the experimental details for the subsequent methods. All materials, unless otherwise stated, were obtained from Sigma Aldrich.

Conjugation

Nanoparticles were conjugated to thyroglobulin following the methods Proc. Natl. Acad. Sci. USA Vol. 95, pp. 10809-10813, September 1998. This involved dissolving the approximately 10 mg of each of the compounds in 0.1 mL dry pyridine together with 55 mg N-hydroxysuccinimide. Dicyclohexylcarbodiimide (40 mg) dissolved in 0.1 mL dry pyridine was added to each sample, and the reaction was allowed to proceed at room temperature for 48 hours. The reaction mixture then was added dropwise over a period of about 5 min to 10.4 mg thyroglobulin dissolved in 1 mL of water and adjusted to pH 9.5. The pH was kept at 8.5 throughout the reaction by the addition of 1M $NaHCO_3$. Some turbidity appeared during the reaction. The reaction was allowed to proceed for 4 hours and the mixture was then dialyzed against PBS overnight at 4° C.

Immunization

Each sample was aliquoted into eight tubes, two of which had twice as much antigen as the others, for primary immunizations. The primary immunizations were emulsified in Freund's complete adjuvant, and then the three subsequent booster immunizations were emulsified in Freund's incomplete adjuvant. Two hens were with each type of nanoparticle immunized by Gallus Immunotech Inc (Fergus, Canada) according to the schedule outlined in Appendix B. The method involves collecting a couple of eggs from each hen before immunization begins, to purify the IgY as the preimmune control. On day 0, each hen was injected with approximately 1 mg antigen (with Freund's complete adjuvant), subcutaneously and/or intramuscularly into the breast tissue of the hen at multiple sites. The total volume of antigen/adjuvant is about 1 mL with the adjuvant making up between half and two-thirds the volume. The immunization was repeated on day 10, 20 and 30 using incomplete Freund's adjuvant and about half the amount of antigen. On day 37, eggs were collected for ten days, for purification of IgY.

An example immunization schedule is shown below:

Primary immunization in Freund's complete adjuvant

Booster 1 (10 days later in Freund's incomplete adjuvant)

Booster 2 (10 days later in Freund's incomplete adjuvant)

Booster 3 (11 days later) Mar. 25, 2011 in Freund's incomplete adjuvant)

Production Schedule:

Immune egg collection: starting 7 days later

Egg yolk IgY purification: starting about 10 days later

Delivery: about 7 days later.

The egg yolks from hens immunized with each antigen were combined, and purified using a two step process, by Gallus Immunotech Ltd using the IgY EggsPress Purification Kit. This involves a first step of incubating with the delipidation agent which removes most of the lipids and lipoproteins, leaving a water soluble fraction containing IgY along with other proteins. Following the delipidation of the egg yolk, the almost lipid-free solution was then treated to concentrate/purify the IgY fraction. This resulted in a IgY preparation that is 85-90% pure. The IgY was resuspended in PBS, at pH 7.3 with 0.05% sodium azide as a preservative agent. The yields were determined by absorbance spectroscopy, and are reported in the results section for each preparation.

ELISA

Binding studies were conducted to determine the specific binding activity of each of the IgY preparations for the different types of nanoparticle. These assays involved adsorbing the nanoparticles to the surface of 96-well plates (Nunc-Immuno™) at a fixed concentration. For initial experiments, this was achieved by placing 100 ng of each nanoparticle (i.e. 200 μL of 0.5 mg/mL stock in PBS) in each well and incubating overnight at 4° C. Later, this was altered to incubate nanoparticles in wells at room temperature for 48 hours until all liquid had evaporated. This was followed by washing wells three times with PBS, and incubating with blocking buffer (PBS with 0.05% Tween-20 and 2% non-fat milk powder). Blocking was done overnight at 4° C. The plates were washed again three times with PBS with 0.05% Tween-20 (PBS/T) and then incubated with different titrations of the IgY antibodies, or matched pre-immune controls (all added at 200 μL per well), diluted in blocking buffer for 2 hours at room temperature. For the specificity binding assays where multiple antibodies were tested against a single antigen immobilized on given plate, the antibody concentration used was 0.5 mg/mL, for both the IgY and pre-immune controls. The plates were washed again three times with PBS/T, and then incubated with 200 μL of a 1:2000 dilution of the peroxidase-conjugated rabbit anti-Chicken IgY secondary antibody (Sigma A9046) for 1 hour at room temperature. Plates were then washed again three times with PBS/T and developed using o-phenylenediamine dihydrochloride in urea buffer (SigmaFast OPD; Sigma P9187), for approximately 15 mins, stopped with 100 μL of a 0.5M oxalic acid solution. Plates were then read on an absorbance spectrophotometer at 492 nm. Specific binding was determined as the difference between absorbance readings for wells with IgY compared to their matched pre-immune controls. Each data point was conducted in triplicate and the average and standard deviation are shown in the graphs in the figures (FIGS. 1-12).

Assays

To determine whether the IgY antibodies could effectively remove nanoparticles from solution, the following assay was conducted. Nanoparticles were suspended in PBS at a concentration of 0.5 mg/mL, aliquoted into microcentrifuge tubes. Note, this is only an approximate concentration, as not all nanoparticles were completely suspended, even after shaking for 48 hours at room temperature. Absorbance measurements were conducted using a Thermo Scientific NanoDrop 2000c spectrophotometer, to determine relative concentrations. Tubes were centrifuged in a Stratagene PigoFuge® microcentrifuge for 10 seconds before each measurement. To each suspension of nanoparticles, IgY was titrated at the concentrations shown below, incubated for 5 minutes at room temperature to allow for binding, and successive absorbance measurements made. Control measurements were made with IgY added alone to account for background fluorescence due to the proteins.

To determine whether filtration of the nanoparticles could be enhanced using the antibodies, a number of types of filters were used. For example, Pall AcroWell 96-well filter plates with 0.45 µm pore size filters were loaded with nanoparticles at 0.5 mg/mL, with or without 2 mg/mL of IgY. These plates were centrifuged at 800 g for 5 minutes, and eluates collected in the bottom 96-well plate. However, these filters removed all nanoparticles from solution, including those without IgY, most likely due to aggregation of the nanoparticles in PBS. Bench experiments with filters with larger pore size resulted in similar results, even with much larger pore sizes. Presumably the aggregates are effectively filtered by most filters due to being in suspension.

Results of Immunizations

All immunizations resulted in an increase in IgY concentration in preparations, compared to pre-immunization levels (see Table 2). This indicated that all immunizations caused an immune response in the hens. Pre-immune protein was collected and IgY fraction purified according to Gallus Immunotech's procedure using two eggs from each chicken prior to immunization. Each antigen was used to immunize two hens, and ten eggs were collected from each to prepare the IgY fractions (approximately 90% pure IgY).

TABLE 2

| Antigen | Pre-immune protein concentration | Post-immune protein concentration | Post immune volume | IgY amount* |
|---|---|---|---|---|
| $C_{60}$ | 11.5 mg/mL | 23.4 mg/mL | 43 mL | 905 mg |
| SWCNT | 9.2 mg/mL | 20.7 mg/mL | 49 mL | 913 mg |
| DPM | 11.6 mg/mL | 22.5 mg/mL | 45 mL | 911 mg |
| $Al_2O_3$ | 10.0 mg/mL | 22.5 mg/mL | 45 mL | 911 mg |
| $TiO_2$ | 14.3 mg/mL | 21.9 mg/mL | 46 mL | 907 mg |
| Amosite | 16.9 mg/mL | 22.8 mg/mL | 44 mL | 903 mg |

*assuming 90% purity

Example 2

Anti-$C_{60}$ IgY

Chickens were immunized with $C_{60}$, and antibodies were isolated as described in Example 1. Specific binding of isolated anti-$C_{60}$ IgY antibody to Ag-conjugated $C_{60}$ was measured by ELISA as described in Example 1. Removal of nanoparticles from solution was assayed as described in Example 1.

As shown in FIG. 1, the titration of the anti-$C_{60}$ IgY and pre-immune controls, binding to immobilized $C_{60}$ antigen demonstrates a good titration with significant specific binding activity (noted as the increase in binding of IgY over pre-immune at a given concentration of antibody).

Figure 2:
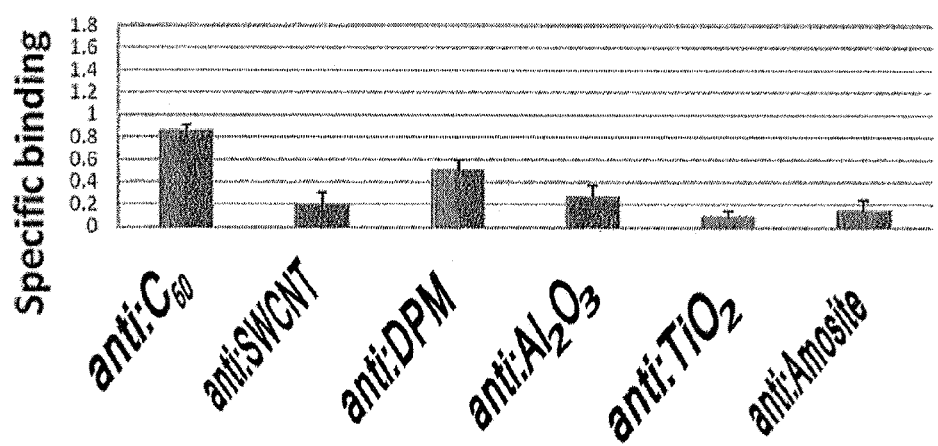
FIG. 2 is a bar chart depicting the results of antibody binding to immobilized $C_{60}$ Ag.

FIG. 2 shows the specific binding (i.e. IgY minus pre-immune control), of all the IgY preparations, binding to immobilized $C_{60}$ antigen. This demonstrates that the specific binding of the anti-$C_{60}$ IgY was higher than any other antibody, indicating a specific interaction.

Figure 13:
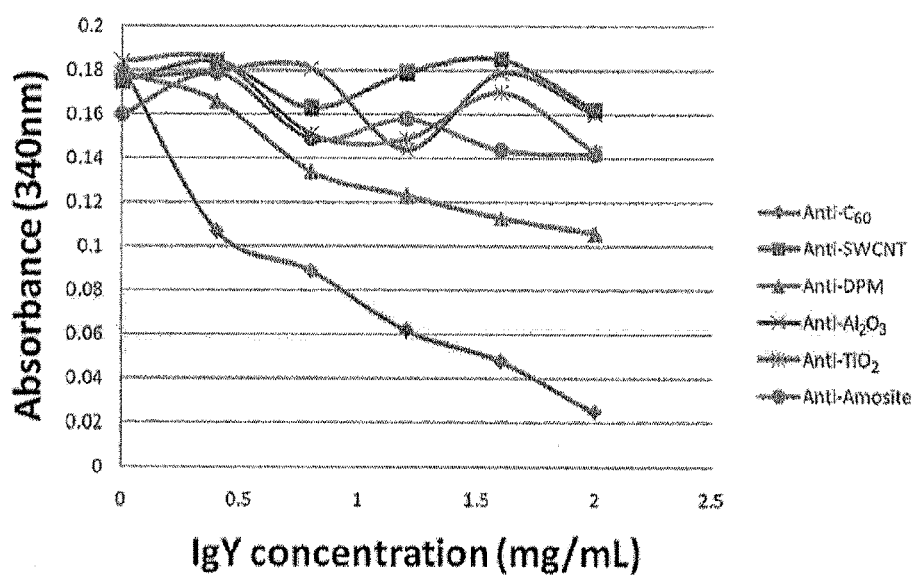
FIG. 13 is a graph depicting the results of precipitation of $C_{60}$ in suspension by IgY.

FIG. 13 shows that there was a significant reduction in the amount of C60 in suspension when increasing amounts of anti-$C_{60}$ IgY were added to the solution. The anti-DPM antibodies also showed some precipitation of $C_{60}$, but to a lesser extent.

Example 3

Anti-SWCNT IgY

Chickens were immunized with single-walled carbon nanotubes (SWCNT), and antibodies were isolated as described in Example 1. Binding of isolated anti-SWCNT IgY antibody to Ag-conjugated SWCNT was measured by ELISA as described in Example 1. Removal of nanoparticles from solution was assayed as described in Example 1.

Figure 3:
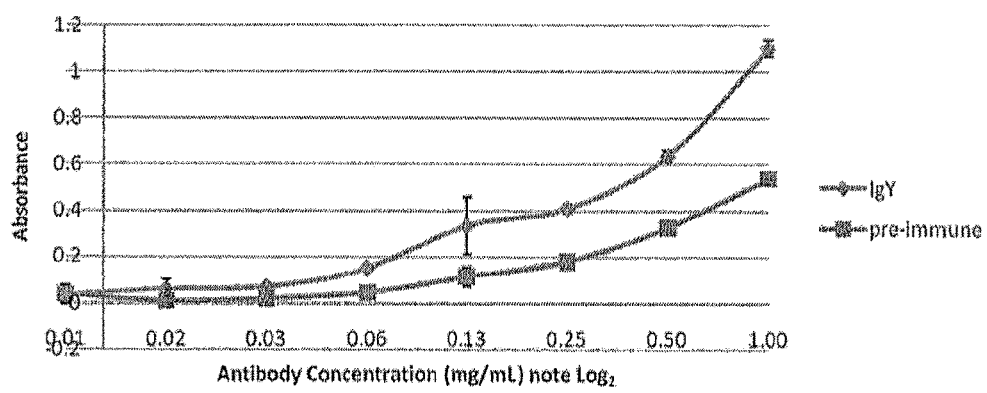
FIG. 3 is a graph depicting the results of anti-SWCNT IgY binding to SWCNT Ag (SWCNT=single-walled carbon nanotube).
Figure 4:
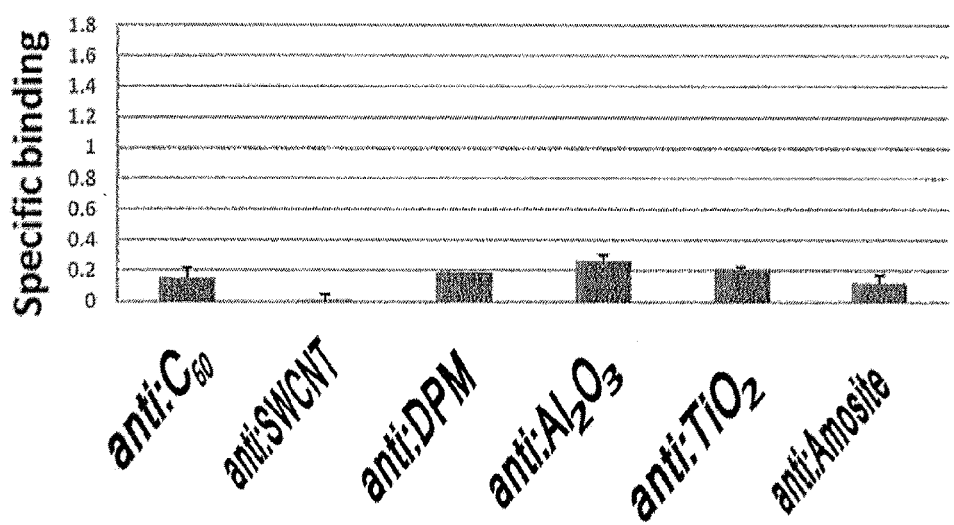
FIG. 4 is a bar chart depicting the results of antibody binding to immobilized SWCNT Ag.

As shown in FIG. 3, there was only a small difference between the amount of IgY binding and pre-immune control at each concentration for the binding to the single-walled carbon nanotubes (SWCNT). This suggests that the specific interaction of the IgY was somewhat weak for this antibody, and is supported by the comparison of all antibodies binding to the Ag-immobilized SWCNT (FIG. 4), demonstrating lower specific activity of any of the antibodies.

Figure 14:
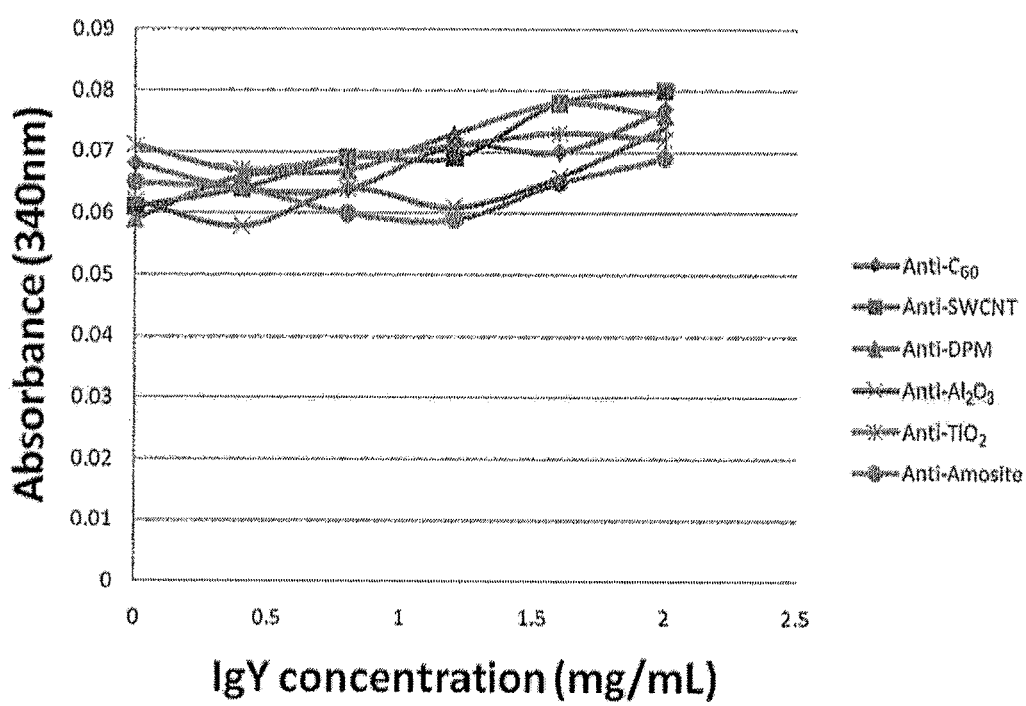
FIG. 14 is a graph depicting the results of SWCNT in suspension.

As shown in FIG. 14, there was no observable precipitation from suspension of the SWCNT by any of the antibodies at the concentrations used.

Example 4

Anti-Diesel Particulate Matter (DPM) IgY

Chickens were immunized with diesel particulate matter (DPM), and antibodies were isolated as described in Example 1. Binding of isolated anti-DPM IgY antibody to Ag-conjugated DPM was measured by ELISA as described in Example 1.

Figure 5:
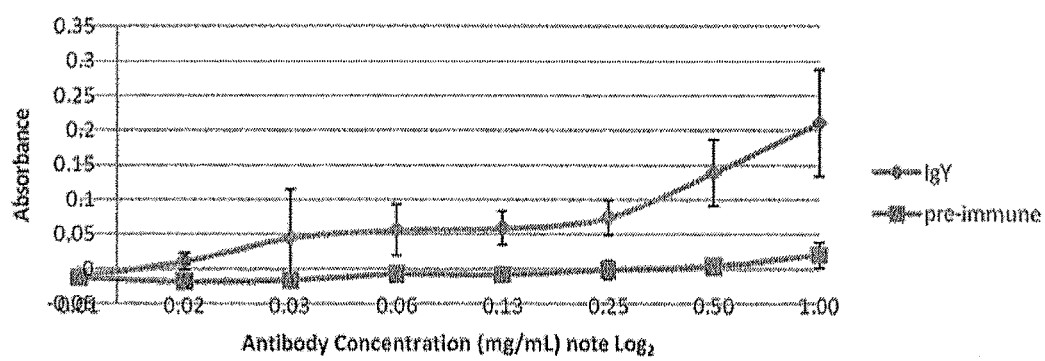
FIG. 5 is a graph depicting the results of anti-DPM IgY binding to DPM Ag (DPM=Diesel Particulate Matter).

Removal of nanoparticles from solution was assayed as described in Example 1. As shown in FIG. 5, the anti-DPM antibodies did demonstrate some specific binding. It is noted that the standard deviations in these experiments were higher, and this is due to the difficulty in immobilizing these nanoparticles with the procedure. Modification of the adsorption of the particles to the wells was done in subsequent experiments.

Figure 6:
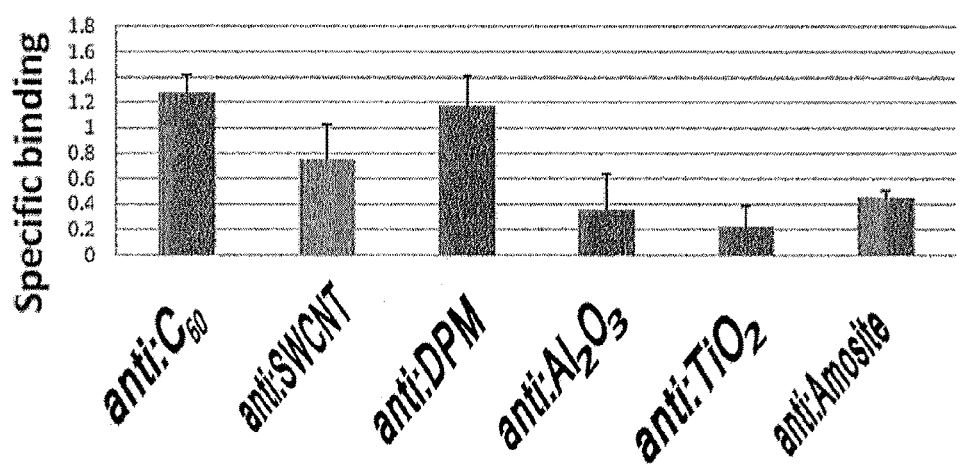
FIG. 6 is a bar chart depicting the results of binding to immobilized DPM Ag.

As shown in FIG. 6, comparing all antibodies binding to immobilized DPM for specific binding revealed that the anti-DPM antibody was selective, in that it had the highest specific binding of the group. The anti-$C_{60}$ and anti-SWCNT also demonstrated elevated specific binding, especially compared to the antibodies against inorganic compounds.

Figure 15A:
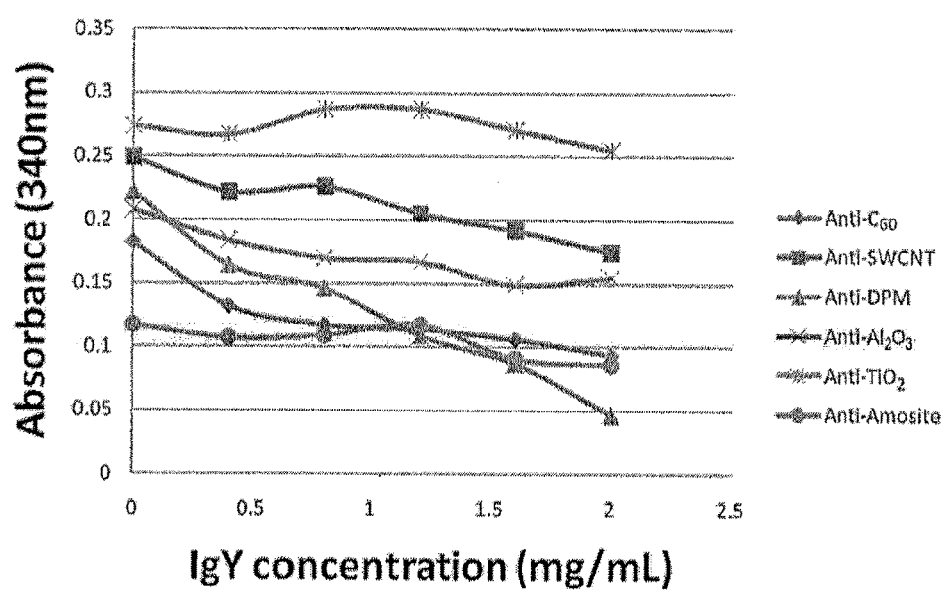
FIG. 15($a$) is a graph depicting the results of antibody precipitation of DPM in suspension.
Figure 15B:
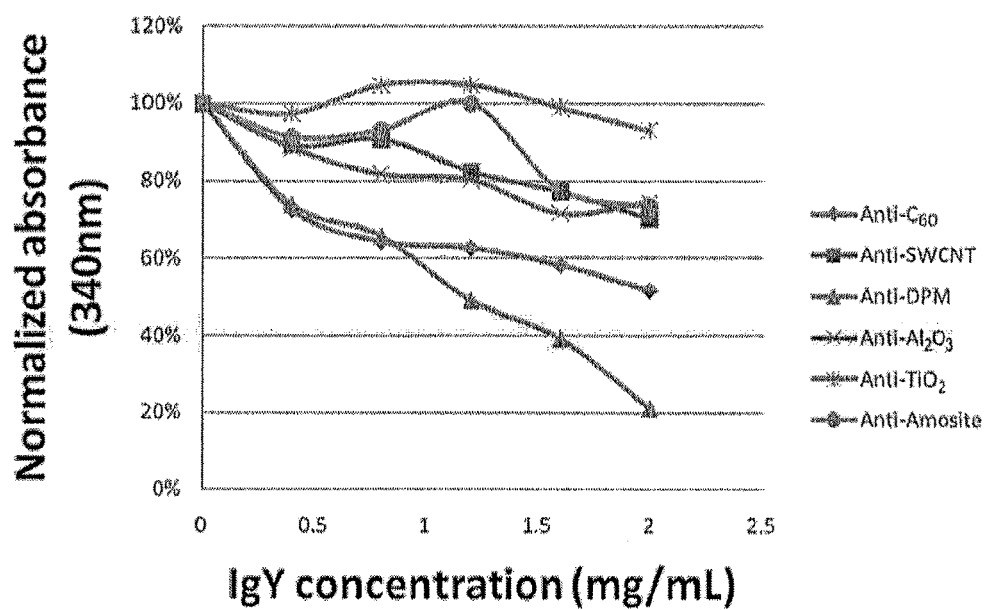

As shown in FIG. 15(a), there was significant variability in the absorbance readings for the DPM in solution. However, after normalization (see FIG. 15b), comparing the absorbance levels to those without antibody, a significant reduction in the amount of DPM was noted for titrations of both anti-DPM and to a lesser extent, the anti-$C_{60}$ antibodies.

Example 5

Anti-$Al_2O_3$ IgY

Chickens were immunized with $Al_2O_3$, and antibodies were isolated as described in Example 1. Binding of isolated anti-$Al_2O_3$ IgY antibody to Ag-conjugated $Al_2O_3$ was measured by ELISA as described in Example 1. Removal of nanoparticles from solution was assayed as described in Example 1.

Figure 7:
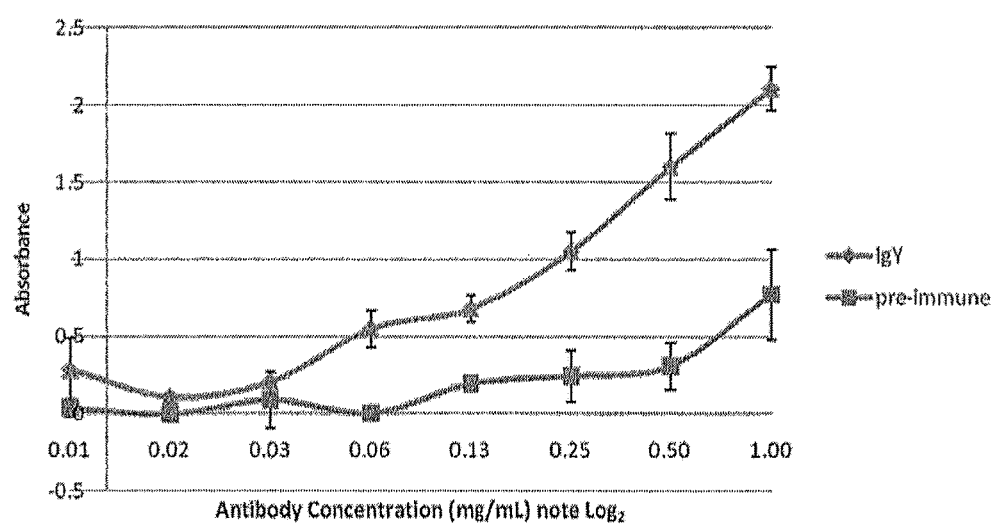
FIG. 7 is a graph depicting the results of anti-$Al_2O_3$ IgY binding to $Al_2O_3$ Ag.
Figure 8:
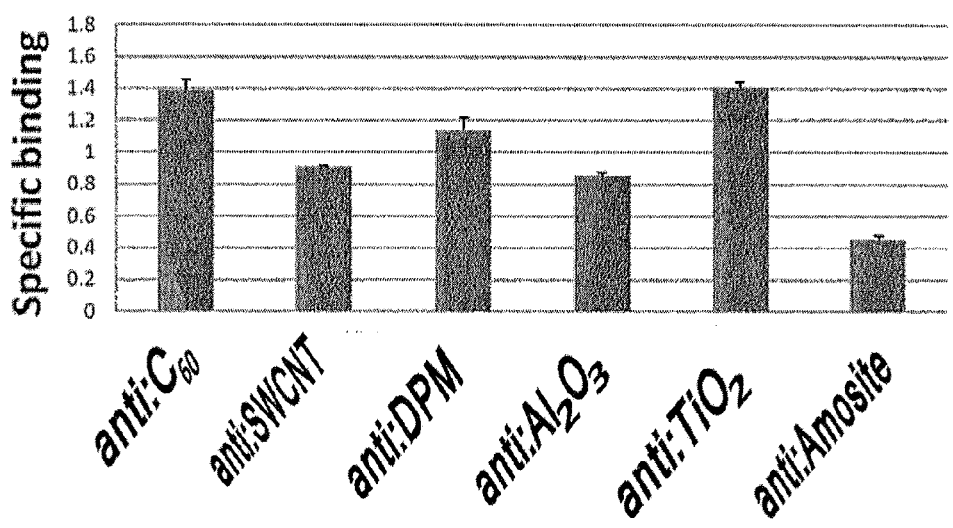
FIG. 8 is a bar chart depicting the results of binding to immobilized $Al_2O_3$ Ag.

As shown in FIG. 7, the anti-$Al_2O_3$ IgY displayed an increased binding to immobilized $Al_2O_3$ compared to matched pre-immune IgY. However, when all the antibodies were tested for binding to immobilized $Al_2O_3$ it was found that most had high binding to these particles, and that the anti-Al$_2$O$_3$ was not the most avid (see FIG. 8).

Figure 16:
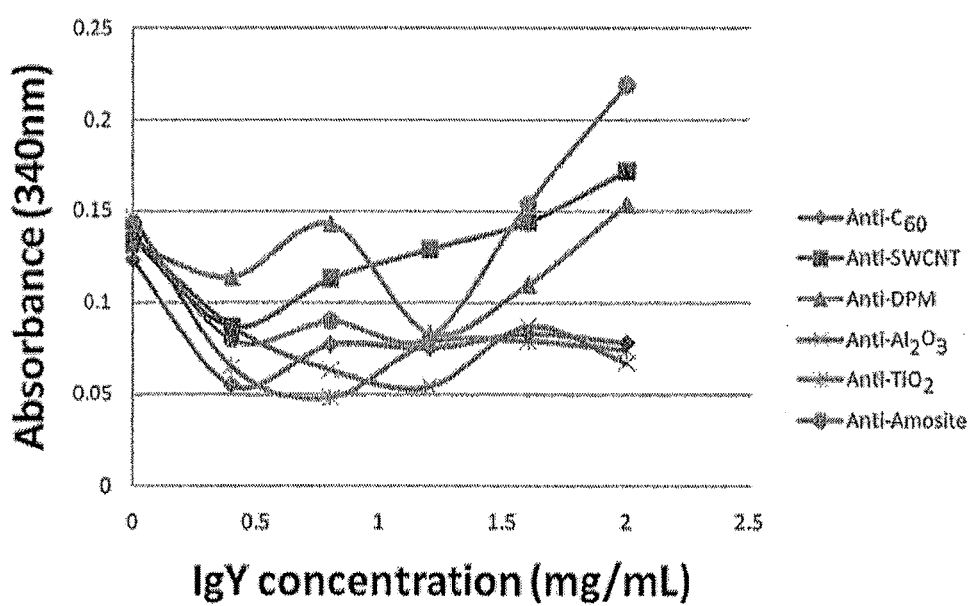
FIG. 16 is a graph depicting the results of antibody precipitation of $Al_2O_3$ in suspension.

As shown in FIG. 16, there was considerable removal of Al$_2$O$_3$ by most antibodies, albeit not complete, and with considerable variability. This suggests there may be a non-specific interaction of these particles with the antibody preparations.

Example 6

Anti-TiO$_2$ IgY

Chickens were immunized with TiO$_2$, and antibodies were isolated as described in Example 1. Binding of isolated anti-TiO$_2$ IgY antibody to Ag-conjugated TiO$_2$ was measured by ELISA as described in Example 1. The anti-TiO$_2$ antibodies were not tested in the precipitation assay (as the particles would not solubilise in buffers which would be compatible to antibody binding).

Figure 9:
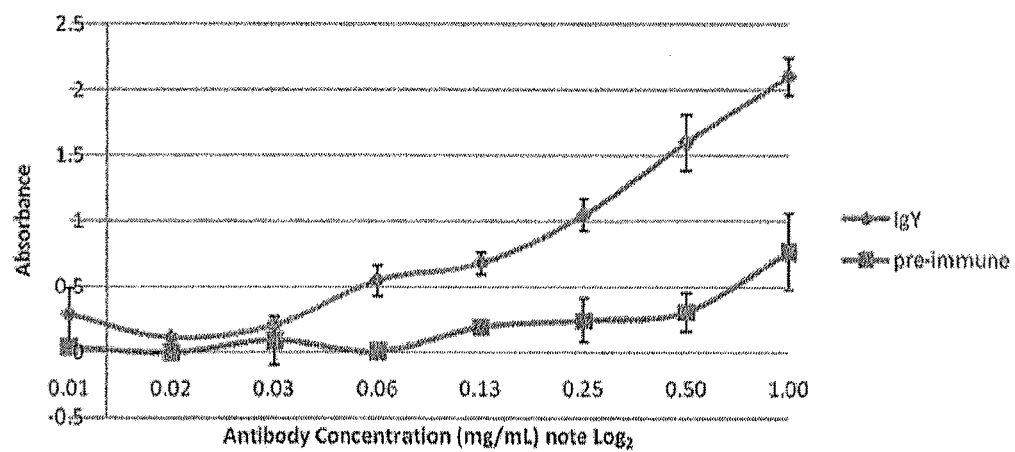
FIG. 9 is a graph depicting the results of anti-$TiO_2$ IgY binding to $TiO_2$ Ag.
Figure 10:
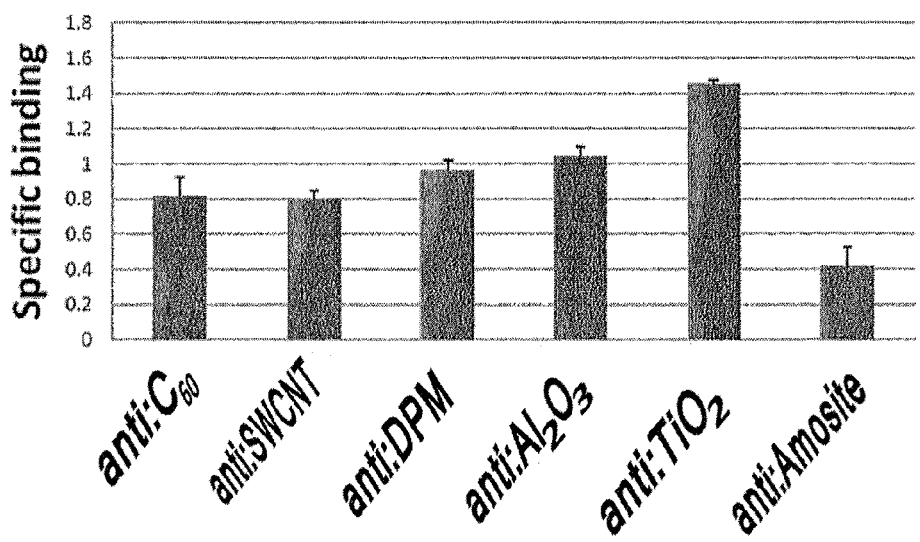
FIG. 10 is a bar chart depicting the results of binding to immobilized $TiO_2$ Ag.

As shown in FIG. 9, there was higher binding for the anti-TiO$_2$ antibodies compared to the pre-immune control. FIG. 10 shows that this antibody bound specifically to immobilized TiO$_2$ more avidly than the other antibodies.

Example 7

Anti-Amosite IgY

Chickens were immunized with amosite (brown asbestos), and antibodies were isolated as described in Example 1. Binding of isolated anti-amosite IgY antibody to Ag-conjugated amosite was measured by ELISA as described in Example 1. The anti-amosite antibodies were not tested in the precipitation assay as it was difficult to solubilize these particles in buffers which would be compatible to antibody binding.

Figure 11:
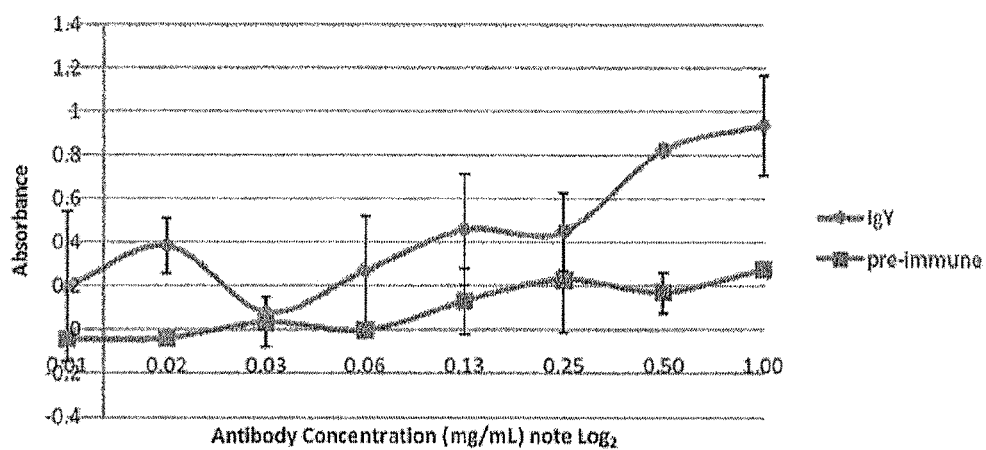
FIG. 11 is a graph depicting the results of anti-Asbestos (amosite) IgY binding to Asbestos (amosite) Ag.
Figure 12:
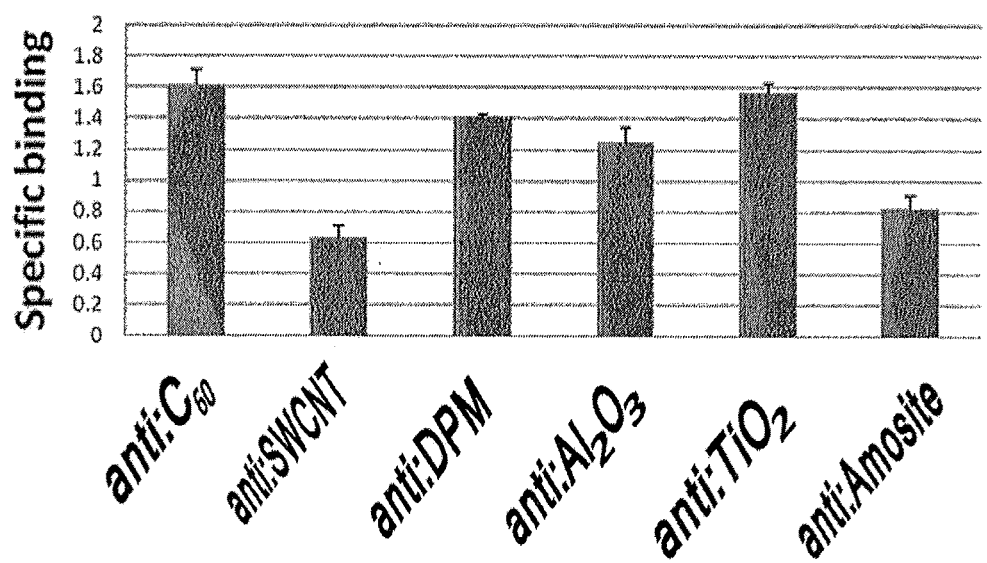
FIG. 12 is a bar chart depicting the results of binding to immobilized Amosite Ag.

As shown in FIG. 11, there was little specific binding for the anti-amosite antibodies compared to the pre-immune control. The high standard deviations most likely are reflective of variability in the immobilization of the antigen to the wells, as this was a difficult particle to solubilize. The anti-amosite antibody did not appear to be specifically binding the amosite antigen, as there was a high level of binding detected across most of the antibodies, as illustrated in FIG. 12.

Discussion of Examples 1-7

Table 3, below, summarizes the collective findings discussed above. While all nanoparticle formulations raised an immune response in the hens, only antibodies against C$_{60}$, DPM, TiO$_2$ and Amosite demonstrated a strong specific binding to the antigen used as the immunogen. Of these, however, only C$_{60}$, DPM and TiO$_2$ demonstrated that the binding was specific for their immunogen, compared to the other antibodies. While it was not possible to test the TiO$_2$ in the precipitation assay applied, both antibodies for C$_{60}$ and DPM demonstrated a specific ability to remove these antigens from solution.

TABLE 3

Summary of Examples 1-7.

| Antigen | Antibody Raised | Binding to Antigen | Specific Binding to Antigen | Ability to specifically remove particle from solution |
|---|---|---|---|---|
| C$_{60}$ | + | + | + | + |
| SWCNT | + | +/− | − | − |
| DPM | + | + | + | + |
| Al$_2$O$_3$ | + | − | − | − |
| TiO$_2$ | + | + | + | ND |
| Amosite | + | + | − | ND |

As noted in Table 3 above, specific antibodies were obtained C$_{60}$, DPM and TiO$_2$. The SWCNT did not seem to raise specific antibodies with the formulation given. A reformulation of these nanoparticles could sufficiently present them to the immune system of the hens. Interestingly, none of the other antibodies seemed to specifically bind the immobilized SWCNT in the binding assays. Since C$_{60}$ and SWCNTs are made of substantially the same material, this result demonstrates that the binding of the C$_{60}$ antibodies to C$_{60}$ is able to discriminate the shape of the fullerenes, from the shape of graphene arranged into a nanotube. There was some overlap between binding of antibodies formed against C$_{60}$ and DPM for each of the antigens. This confirms that there is significant epitope similarity across these two immunogens. Antibodies raised against the inorganic nanoparticles were less avid binders of the carbon nanoparticles, which demonstrates that there is significant material discrimination in the chicken immune response as well, reflected in the antibodies produced.

Antibodies against aluminum oxide nanoparticles were not specific, and it was noted that most antibodies bound to these nanoparticles. Thus, these nanoparticles are not suitable for generating specific antibodies in this manner, as it seemed there is significant non-specific binding of these particles to many proteins. However, as antibodies were generated, it does appear that nonspecific antibodies can be generated in the noted manner.

Antibodies against TiO$_2$ did seem to raise a highly specific response, and although these particles display non-specific binding, there was an increased binding for their antibodies compared to the others. This demonstrates that it is possible to raise antibodies against inorganic nanoparticles. The antibodies against C$_{60}$ and DPM were successfully demonstrated to be able to specifically remove their respective particles from solution after binding and centrifugation. In some embodiments, a secondary antibody, or crosslinking the antibodies, or tether the IgY to a larger particle such as a magnetic particle or agarose bead, can be used to remove the bound nanoparticles from solution by precipitation. However, this was not necessary for C$_{60}$, and most nanoparticles were removed with about 4× excess of IgY preparation added.

The preparations of antibodies in the above examples are about 90% IgY, but include a polyclonal response, as well as all other IgY's that the chicken is producing. In some embodiments, the above results can be improved further by, for example, affinity purifying these preparations (the specific activity of the preparations would likely increase significantly, although yields would be diminished concomitantly). Further improvements can be obtained by making monoclonal antibodies against specific epitopes of different nanoparticles, which would significantly increase the specificity of responses.

It is noted that the inability in the above Examples to raise a specific response to some of the nanoparticles can be due to an inappropriate formulation of the antigens, as opposed to an inability of the chicken's immune response to produce antibodies which can recognize these particles. It is predicted that this can be overcome by providing a different conjugate, and/or crosslinking the nanoparticles to the conjugates in a different way. Regardless, the above data demonstrate the ability to raise an immune response against both organic and inorganic nanoparticles.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

What is claimed is:

1. An isolated chicken antibody or binding fragment thereof that specifically binds to a nanoparticle, wherein the antibody or binding fragment thereof binds specifically to at least one of: a crystalline form of $TiO_2$, a diesel particulate, and an asbestos fiber.

2. The isolated chicken antibody or binding fragment of claim 1, wherein the antibody or binding fragment thereof comprises an IgY antibody.

3. The isolated chicken antibody or binding fragment of claim 2, wherein the nanoparticle has a diameter of about 1 nanometers to about 10,000 nanometers.

4. The isolated chicken antibody or binding fragment of claim 3, wherein the antibody or binding fragment thereof binds specifically to an asbestos fiber.

5. An isolated antibody or binding fragment thereof that binds specifically to a nanoparticle, wherein the nanoparticle comprises at least one of: a crystalline form of $TiO_2$, a diesel particulate, and an asbestos fiber, wherein the antibody or binding fragment thereof is a chicken antibody.

6. The isolated antibody or binding fragment of claim 5, wherein the antibody or binding fragment thereof is a monoclonal antibody.

7. The isolated antibody or binding fragment of claim 5, wherein the antibody or binding fragment thereof comprises a heavy chain chicken framework region 1.

8. The isolated antibody or binding fragment of claim 5, wherein the antibody or binding fragment thereof comprises a heavy chain chicken framework region 2.

9. The isolated antibody or binding fragment of claim 5, wherein the antibody or binding fragment thereof comprises a heavy chain chicken framework region 3.

10. The isolated antibody or binding fragment of claim 5, wherein the antibody or binding fragment thereof comprises a heavy chain chicken framework region 4.

11. The isolated antibody or binding fragment of claim 5, wherein the antibody or binding fragment thereof comprises a chicken constant domain.

12. The isolated antibody or binding fragment of claim 11, wherein the antibody or binding fragment thereof comprises a chicken variable domain.

13. An antibody composition comprising:

at least one chicken antibody or binding fragment thereof that specifically binds to a nanoparticle, wherein the nanoparticle comprises at least one of: a crystalline form of $TiO_2$, a diesel particulate, and an asbestos fiber; and at least one compound selected from the group consisting of: an aerosolizing medium, a sprayable medium, a cross-linker, a support surface, a fiber, a foam medium, a pharmaceutically acceptable carrier, a magnetic particle, a lotion, and any combination thereof.

14. The antibody composition of claim 13, wherein the antibody or binding fragment thereof specifically binds to an asbestos fiber.

15. The antibody composition of claim 13, wherein the antibody or binding fragment thereof is immobilized on the support surface.

16. The antibody composition of claim 15, wherein the support surface comprises a filter.

17. The antibody composition of claim 13, wherein the pharmaceutically acceptable carrier is at least one of a lozenge, a candy, a chewing gum, a mouthwash, or a mouth spray.

18. A composition for targeting a nanoparticle for delivery to an immune system, the composition comprising:

at least one nanoparticle, wherein the nanoparticle comprises at least one of: a crystalline form of $TiO_2$, a diesel particulate, and an asbestos fiber; and at least one chicken antibody or binding fragment thereof that specifically binds to the at least one nanoparticle.

19. An array comprising:

a support; and at least one chicken antibody or binding fragment thereof that binds specifically to a nanoparticle, wherein the nanoparticle comprises at least one of: a crystalline form of TiO2, a diesel particulate, and an asbestos fiber, wherein the at least one chicken antibody or fragment thereof is immobilized on the support.

20. An isolated chicken antibody or binding fragment thereof that selectively binds to a nanoparticle based upon a material of the nanoparticle, wherein the nanoparticle comprises at least one of: a crystalline form of $TiO_2$, a diesel particulate, and an asbestos fiber.

21. The isolated chicken antibody of claim 20, wherein the antibody selectively binds to carbon.

22. The isolated chicken antibody of claim 20, wherein the antibody selectively binds to silicate.

23. An isolated chicken antibody or binding fragment thereof that specifically binds to an epitope on a nanoparticulate, wherein the nanoparticle comprises at least one of: a crystalline form of $TiO_2$, a diesel particulate, and an asbestos fiber.

24. The antibody of claim 23, wherein the larger structure has a diameter of 10 to 1,000,000,000 nm.

* * * * *

UNITED STATES PATENT AND TRADEMARK OFFICE
CERTIFICATE OF CORRECTION

| | | |
|---|---|---|
| PATENT NO. | : 9,228,025 B2 | Page 1 of 1 |
| APPLICATION NO. | : 13/695276 | |
| DATED | : January 5, 2016 | |
| INVENTOR(S) | : Manion | |

It is certified that error appears in the above-identified patent and that said Letters Patent is hereby corrected as shown below:

Specification

In Column 1, Line 8, delete "§371" and insert -- § 371 --, therefor.

In Column 16, Line 64, delete "PigoFuge®" and insert -- PicoFuge® --, therefor.

In Column 18, Line 49, delete "(see FIG. 15b)," and insert -- (see FIG. (15b)), --, therefor.

Claims

In Column 24, Line 8, in Claim 19, delete "TiO2," and insert -- $TiO_2$, --, therefor.

Signed and Sealed this
Nineteenth Day of April, 2016

Michelle K. Lee
*Director of the United States Patent and Trademark Office*